United States Patent [19]

Maryanoff et al.

[11] Patent Number: 4,693,850
[45] Date of Patent: Sep. 15, 1987

[54] METHANE SULFONIC ACID DERIVATIVES

[75] Inventors: Cynthia A. Maryanoff, Solebury Township, Bucks County; James N. Plampin, Roslyn; Robin C. Stanzione, West Chester, all of Pa.

[73] Assignee: McNeilab, Inc., Fort Washington, Pa.

[21] Appl. No.: 935,667

[22] Filed: Nov. 26, 1986

Related U.S. Application Data

[62] Division of Ser. No. 711,948, Mar. 15, 1985, Pat. No. 4,656,270.

[51] Int. Cl.$^4$ ............................................. C07C 143/56
[52] U.S. Cl. .................................... 260/506; 544/165; 544/167; 549/439; 560/142
[58] Field of Search ...................... 549/439; 560/142; 260/506

[56] References Cited

U.S. PATENT DOCUMENTS

| 4,210,658 | 7/1980 | Durant et al. | 548/138 |
| 4,265,896 | 5/1981 | Durant et al. | 546/275 |
| 4,381,395 | 4/1983 | Teraji et al. | 548/342 |

FOREIGN PATENT DOCUMENTS 1587258  4/1981  United Kingdom .

OTHER PUBLICATIONS

Walter et al, Liebigs Ann. Chem., 722, pp. 98–109 (1969).
Yarovenko et al, Chemical Abstracts, vol. 76, No. 59163c (1972).

Primary Examiner—Robert W. Ramsuer
Attorney, Agent, or Firm—David J. Levy

[57] ABSTRACT

Novel synthetic steps and intermediates leading to guanidines such as the anti-diabetic compound linogliride. Included is a hydrogen peroxide oxidation of a thiourea (II) to a sulfonic acid (I) which may then be reacted with morpholine to form the carboximidamide (III):

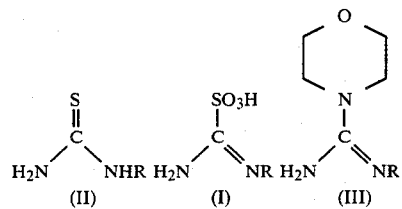

5 Claims, No Drawings

METHANE SULFONIC ACID DERIVATIVES

This division of U.S. patent application Ser. No. 711,948, filed Mar. 15, 1985, now U.S. Pat. No. 4,656,270.

BACKGROUND OF THE INVENTION

The present invention relates to the synthesis of guanidine compounds such as the anti-diabetic compound linogliride or N-(1-methyl-2-pyrrolidinylidene)-N'-phenyl-4-morpholinecarboximidamide and includes synthetic steps and intermediates.

Linogliride fumarate (CAS Registry No. 78782-47-5) is a hypoglycemic compound and is disclosed in U.S. Pat. No. 4,211,867. It is an object of the present invention to provide a high yield, facile and short synthesis of linogliride with byproducts and reagents which are comparatively safe and easily handled.

At column 11 of U.S. Pat. No. 4,211,867 there is described a method of making an N,N'-disubstituted guanidine intermediate by reacting an N-substituted thiourea with an alkylating agent to produce the corresponding alkylthio compound which is then reacted with an amine to displace a mercaptan. Such a route has the disadvantage of removal and disposal of odoriferous mercaptans.

Oxidations of thioureas are found in U.S. Pat. Nos. 4,210,658, 4,265,896 and 4,381,395, U.K. Pat. No. 1,587,258, U.S.S.R. Pat. No. 178,803 published Feb. 3, 1966 and by W. Walter and G. Randau in Liebigs Ann. Chem. 722, pages 98–109 (1969).

SUMMARY OF THE INVENTION

A method has been devised whereby N-arylthioureas are oxidized in high yields to N-arylformamidinesulfonic acids by using a molybdenum catalyst such as $Na_2MoO_4$ with $H_2O_2$ as the oxidizing agent. Such sulfonic acids have been found to be excellent intermediates for the preparation of guanidines such as N-phenyl-4-morpholinecarboximidamide, which is itself a precursor for the preparation of linogliride.

DETAILED DESCRIPTION OF THE INVENTION

According to the invention, N-(1-methyl-2-pyrrolidinylidene)-N'-aryl-4-morpholinecarboximidamides of the formula (V), including linogliride, may be prepared according to the following reaction scheme:

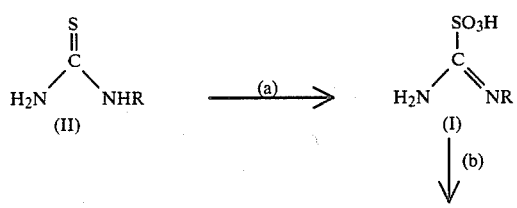

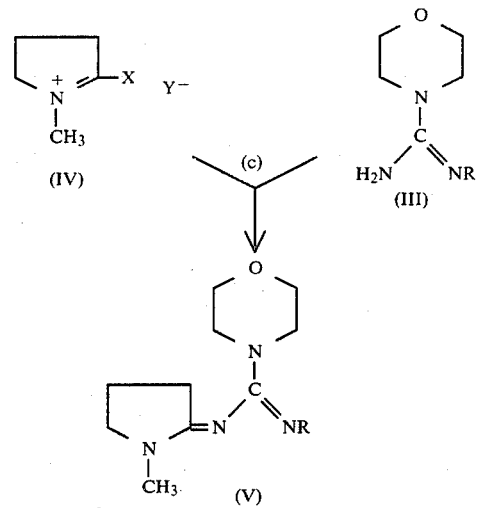

In the above formulae, R is phenyl; methylenedioxyphenyl such as 2,3- or 3,4-methylenedioxyphenyl; phenyl substituted with 1, 2 or 3 substituents independently chosen from the group of halo, such as fluoro, chloro, bromo or iodo, loweralkyl, such as $C_{1-4}$ alkyl including methyl, ethyl and tert-butyl, and lower alkoxy, such as $C_{1-4}$ loweralkyl including methoxy and ethoxy; or phenyl substituted with a single member of the group consisting of dimethylamino, methylethylamino, diethylamino, lower-alkanoylamino such as $C_{1-4}$ alkanoylamino including acetylamino, loweralkylthio such as $C_{1-4}$ alkylthio including methylthio and ethylthio, trifluoromethyl, hydroxy, benzyloxy, loweralkanoyloxy such as $C_{1-4}$ alkanoyloxy including acetoxy, lower alkanoyl such as $C_{1-4}$ alkanoyl including acetyl, and nitro. Single phenyl substitution may be at the 2, 3 or 4 positions while di- and tri-substitution may be at any available position with di- and tri-substitution of the same moiety being preferred over diverse substitution. In particular, R is phenyl or phenyl substituted by a fluorine atom, e.g. 4-fluoro, or a methyl group, e.g. 2-methyl.

The compound of formula (IV) is a lactam salt of 1-methyl-2-pyrrolidinone as described in U.S. Pat. No. 4,211,867. The lactam fluoborates of formula (IV), wherein Y is $BF_4-$, are generally known and may be obtained according to procedures described in the literature, e.g. see Canadian Pat. Nos. 850,116 and 950,464; U.S. Pat. No. 3,876,658; Ber. 89, Page 2063 (1956); and Org. Synth. 46, 113, 120 (1966). The lactam fluorosulfonates of formula (IV), wherein Y— is $OSO_2F-$, are similarly prepared. In general, 1-methyl-2-pyrrolidinone is reacted with an appropriate trialkyl oxonium fluoroborate such as $(CH_3CH_2)_3OBF_4$ or methyl fluorosulfonate to give the corresponding lactam salt. The reaction is preferably carried out from 0°C. to ambient temperature under an inert dry atmosphere (e.g., nitrogen, argon) in an inert anhydrous lower halohydrocarbon solvent such as, for example, chloroform, 1,2-dichloroethane, methylene dichloride (most preferred) and the like. Other inert anhydrous organic solvents that may be employed include ethers such as, for example, diethyl ether, dioxane, tetrahydrofuran (THF), 1,2-dimethoxyethane and the like; and aromatic hydrocarbons such as, for example, benzene, toluene, xylene and the like. Alternatively, the corresponding 2-loweralkylthiolactim ethers where X is S-loweralkyl may be prepared by reaction of 1-methyl-2-pyrrolidinone with $P_2S_5$ according to the procedure of R. Gompper and W. Elser, Org. Syn., Coll. Vol. V, pages 780–783, to yield 1-methyl-2-pyrrolidinthione. Treatment of this thiolactam with loweralkylating agent such as methyliodide, methyl fluorosulfonate, dimethyl sulfate, methyl tosylate, methyl mesylate, and the like, yields the desired 2-loweralkylthiolactim ethers as the corresponding salts. An alternative method of preparing the formula (IV) compounds is by the interaction of 1-methyl-2-pyrrolidinone with dimethyl sulfate to give the corresponding methosulfate salt according to the reaction conditions described by Bredereck et al., Chem. Ber. 96, 1350 (1963). The reaction is preferably carried out in an anhydrous inert organic solvent such as, for example, an aromatic hydrocarbon, e.g. benzene, toluene, xylene and the like, an ether e.g. tetrahydrofuran, dioxane and the like, or a halocarbon, e.g., 1,2-dichloroethane, chloroform and the like. Another method of activating 1-methyl2-pyrrolidinone is by reaction of the methosulfate salt, i.e., formula (IV) where X is $-OCH_3$ and Y is $OSO_3CH_3$— with an alkali metal loweralkoxide, preferably sodium methoxide or sodium ethoxide in the corresponding loweralkanol solvent, according to the reaction conditions described by H. Bredereck, et al., Chem. Ber., 97, 3081–3087 (1964), to yield the corresponding lactam acetal. Another example of an activated lactam of formula (IV) is the chloride salt wherein X is Cl and Y is $Cl^-$. The chloride salts are readily obtained by activation of 1-methyl-2-pyrrolidinone with phosgene (ClCOCl) or thionyl chloride ($SOCl_2$) according to the directions of W. Jentzsch and M. Seefelder, Chem. Ber., 98, 274 (1965), with the evolution of $CO_2$ or $SO_2$, respectively.

In step (a), the N-arylthiourea of formula (II) is oxidized to the N-arylformamidinesulfonic acid of formula (I) with hydrogen peroxide in the presence of a molybdenum (VI) catalyst. During the reaction, the oxidation state of the Mo will vary. The catalyst is in particular, a molybdate of the formula $OMoO_4$ wherein O is two ions having a +1 valence or one ion having a +2 valence. Specific examples of molybdenum catalysts include $H_2MoO_4$, $(NH_4)MoO_4$ or $Na_2MoO_4$. Such catalysts includes hydrates and other solvates, e.g., $Na_2MoO_4\cdot 2H_2O$ and $H_2MoO_4\cdot H_2O$. It has been found that superior yields of final and intermediate products are obtained by operation of step (a) with a molybdenum (VI) catalyst as opposed to other catalysts which may be considered to be equivalents, e.g. tungsten or chromium. Hvdrogen peroxide is used in step (a) as an aqueous solution such as a 10 to 90% by weight solution, e.g. a 30% solution although other hydrogen peroxide sources such as peracetic acid can be used.

The oxidation requires slightly more than about 3 equivalents of $H_2O_2$ and the reaction may be carried out at about 0° to 80° C. Preferably, the reaction is carried out in two stages which are:

(i) during addition of the hydrogen peroxide at a temperature of about 0° to 15° C., and
(ii) after addition of the hydrogen peroxide at a temperature of about 15° to 80° C.

The oxidation gives the best results when the temperature of the addition of $H_2O_2$ is from about 5° to 10° C. The rate of addition of $H_2O_2$ can usually be increased once about ⅔ of the $H_2O_2$ has been added. During the peroxide addition, it is normal to observe color changes of the reaction mixture from white to green or blue.

After addition of the $H_2O_2$, the temperature may be allowed to rise by the exotherm of the reaction to a maximum of about 80° C. during which the color will revert to an off-white color. Preferably, the maximum temperature is about 60° C. or most preferably about 40° C. In a modification of this procedure, the first two equivalents of the $H_2O_2$ are added at about 0° to 15° C., the cooling bath is removed and the temperature is allowed to rise to about 30° to 50° C., e.g. about 40° C. with the final equivalent being added at a rate to maintain the temperature at about 40° C.

Sodium chloride or other inert salts may be added to the reaction mixture to prevent freezing.

The starting material thiourea of formula (II) may be obtained by reaction of the corresponding aryl isothiocyanate with ammonia as described by A. W. Hoffman in J. Fortschrite Chemie 349 (1858) and Comp. Rend., 47 424 as described in Beilstein Hauptwerke, Volume 12, page 454. The arylisothiocyanates of the formula R—N=C=S, many of which are known, may be prepared according to the extensive processes reported in the literature for making isothiocyanates. For example, they may be obtained from the methodologies reported by M. Bogemann et al. in "Methoden der Organische Chemie Houben-Weyl", Eugen Müller (Ed.), Georg Thieme Verlag (Publi.) Stuttgart, Germany, Vol. 9, page 867–884 (1955); "Preparation des Isothiocyanates Aromatiques" by A. Rasschaert et al., Ind. Chim., Belge, 32, 106 (1967); German Pat. No. 1,300,599; J. Org. Chem., 36, 1549 (1971); U.S. Pat. Nos. 2,395,455 and 3,304,167; French Pat. No. 1,528,249; "A New Synthesis of Aliphatic Isothiocyanates", Angew. Chem. Internat. Ed., 6, 174 (1967); Bull. Chem. Soc. Japan, 48 2981 (1975); Tetrahedron, 29, 691 (1973); Chem. Ber., 101, 1746 (1968); and J. Indian Chem. Soc., 52, 148 (1975).

In step (b), the N-arylformamidinesulfonic acid of formula (I) is reacted with morpholine or an activated form of morpholine such as morpholine acetate. An advantage of the orocess of the invention compared to the use of the corresponding N-arylformamidinesulfinic acid is that the sulfinic acid ($-SO_2H$) requires that an activated form of morpholine be used, e.g. morpholine acetate, or morpholine with an acid catalyst. This, of course, necessitates an extra synthetic step in the reaction of commercially available morpholine to its activated form or the use of an extra reagent. Thus a preferred aspect of the invention step (a) is the production of a sulfonic acid which, in the subsequent step (b), allows reaction with the less expensive reactant morpholine. The use of morpholine also results in a higher yield.

The reaction of the sulfonic acid of formula (I) with morpholine may be carried out with a molar excess of morpholine using morpholine itself as the solvent. Thus, use of the sulfonic acid (I) allowing morpholine as the reagent, results in another economy in the overall process. The reaction temperature may be about 15° to 100° C., depending on the particular reactants, with stirring and a co-solvent such as acetonitrile may be added to aid such stirring. The co-solvent should be inert to the reactants, thus eliminating reactive solvents such as methanol.

Step c) is carried out as described in U.S. Pat. No. 4,211,867. In particular, one may use stochiometric quantities of the salt of formula (IV) and the carboximidamide of formula (III). Suitable anhydrous organic solvents for conducting the reaction include anhydrous aprotic solvents, e.g., ethers, such as, for example, diethylether, tetrahydrofuran, dioxane and the like; lower halogenated hydrocarbons, such as, for example, chloroform, methylene chloride, 1,2-dichloroethane and the like; and aromatic hydrocarbons, such as, for example, benzene, toluene, xylene, and the like. Ambient to 0° C. or higher temperature may be employed depending on the particular reactants. The product (V), in the form of the corresponding HY salt, is converted to the corresponding base form, by conventional means, for example, by treatment with a suitable alkali such as alkali metal or alkaline earth metal hydroxides; carbonates and the like. In particular, a temperature of about 25° to 100° C. may be used when the salt (IV) is the methosulfate salt obtained from 1-methyl-2-pyrrolidinone and dimethyl sulfate. Another method of preparing the formula (V) compounds is by the interaction of the guanidine precursor (III) with a chloride salt of formula (IV) in an anhydrous aprotic solvent, such as, for example, an ether, e.g. diethyl ether, dioxane, THF and the like, a halohydrocarbon, e.g. chloroform, methylene dichloride, 1,2-dichloroethane and the like, and, preferably, an aromatic hydrocarbon, e.g., benzene, toluene, xylene and the like.

In the following Examples and throughout the specification, the following abbreviations may be used: mg (milligrams); g (grams); Kg (kilograms); ml (milliliters); tlc (thin layer chromatography); RT (room temperature); L (liter); ir (infrared); m (moles); ~ (about); min (minutes); hr (hours); IPA (isopropyl alcohol); M (molar); N (normal); mp (melting point); bp (boiling point); MeOH (methanol); EtOH (ethanol); HOAc (acetic acid); and C, H, N, O, etc. (the chemical symbols for the elements). Unless otherwise indicated, all temperatures are reported in °C. (degrees centigrade) and, all references to hydrogen peroxide is aqueous hydrogen peroxide and all references to ether are to diethyl ether.

EXAMPLE A i. Formula (I): R=phenyl

N-phenylthiourea (2 g, 0.013 m), sodium tungstate dihydrate (0.008 g, 0.00002 m), and sodium chloride (0.25 g), were suspended in water (10 ml) and cooled to 0°-5° C. using an ice/salt bath. Aqueous hydrogen peroxide (4.5 ml, 0.044 m, 30%) was added at a rate to keep the temperature less than 10° C. Once the addition was complete, the ice bath was removed and the reaction was allowed to exotherm to 35° C. and the temperature was controlled between 30°-35° C. with an ice bath. Once the exotherm was complete, the reaction was stirred at ambient temperature for 30 min and then cooled and filtered. The filter cake was washed once with 2 ml of ice water. There was thus obtained 1.47 g of the sulfonic acid of formula (I) where R=phenyl (56.3%). The ir spectra corresponded to that of desired product.

ii. Formula (III): R=phenyl

The sulfonic acid product of Example Ai (1.46 g) was added to morpholine (1.3 g, 0.015 m) in acetonitrile (9 ml). The reaction exothermed to 35° C. The reaction was then warmed to 50°-60° C. for 30 min. During this time the reaction became homogeneous. The reaction mixture was concentrated and treated with 3N NaOH until very basic. The precipitate was isolated by filtration. There was obtained 1.38 g of the product of formula (III) where R=phenyl as a white solid (52%). The white solid was 80.6% pure which translates to a 41.9% yield of pure product.

EXAMPLE 1

This example was conducted in a side-by-side manner with Example A using identical conditions:

a. Formula (I): R=phenyl

N-phenylthiourea (2 g, 0.013 m), sodium molybdate dihydrate (0.005 g, 0.00002 m), and sodium chloride (0.25 g), were suspended in water (10 ml) and cooled to 0°-5° C. using an ice/salt bath. Aqueous hydrogen peroxide (4.5 ml, 0.044 m, 30%) was added at a rate to keep the temperature less than 10° C. Once the addition was complete, the ice bath was removed and the reaction was allowed to exotherm to 35° C. and the temperature was controlled between 30°-35° C. with an ice bath. Once the exotherm was complete, the reaction was stirred at ambient temperature for 30 min then cooled and filtered. The filter cake was washed once with 2 ml of ice water. There was obtained 1.87 g of the sulfonic acid of formula (I) where R=phenyl (71.6%). The ir spectra corresponded to that of desired product.

b. Formula (III): R=phenyl

The sulfonic acid product of Example 1a (1.86 g) was added to morpholine (1.3 g, 0.015 m). During the addition the reaction mixture became very thick therefore, acetonitrile (9 ml) was added. The reaction exothermed to 35° C. The reaction was then warmed to 50°-60° C. for 30 min. During this time the reaction became homogeneous. The reaction mixture was concentrated and treated with 3N NaOH until very basic. The precipitate was isolated by filtration. There was obtained 1.7 g of the product of formula (III) where R=phenyl as a white solid (65% yield). The yield of pure product, i.e., when adjusted for purity, was 55.6%.

EXAMPLE 2 a. Formula (I): R=phenyl

In a 3-neck round bottom flask (equipped with an ice/salt bath, a thermometer, dropping funnel, and a mechanical stirrer), N-phenylthiourea (1520 g, 10.0 m), sodium molybdate dihydrate (10.0 g, 0.04 m), sodium chloride (700 g, 12 m) were suspended in 7000 ml of water and cooled to 0° C. Hydrogen peroxide (30%, 3.6 Kg, 31.8 m) was added dropwise at a rate to maintain the temperature between 0°-15° C. Once the addition was complete, the cooling bath was removed and the reaction was warmed to 15° C. The reaction was then permitted to exotherm to 45° C. at which time a cooling bath was applied to control the exotherm (reaction continued to exotherm to 70° C.). Once the reaction exotherm was complete, the reaction was cooled to about 10° C. and filtered. The filter cake was washed with a small amount of ice water. The sulfonic acid (I) was obtained as an off-white solid, mp 155°-157° C.

b. Formula (III): R=phenyl

In a 3-neck round bottom flask (equipped with a mechanical stirrer and a thermometer), morpholine (104 g, 12 m) was treated with the sulfonic acid prepared in Example 2a. The resulting slurry was stirred for 30-40 min during which time it exothermed to 102° C. If the temperature of the reaction does not reach 100° C., heat should be applied until the reaction temperature is about 100° C. Once the reaction reaches this temperature, the reaction is considered complete. Once the reaction temperature dropped to 50° C., warm water was added and the reaction was treated with charcoal and filtered. The mother liquor was treated with NaOH (50%, 1280 g, 16 m, diluted to 20% with ice). Upon vigorous stirring, a white semi-solid precipitated from the solution. The solution was filtered and the filter cake was washed with water. The product was isolated as a white solid in a 56% (1117 g) yield from phenylthiourea. Once the product was filtered, it was dissolved in $CH_2Cl_2$ and any water present was separated away. The organic layer was dried with $MgSO_4$ and concentrated in vacuo. The yield reported is based on the product isolated after the water was removed.

EXAMPLE 3 a. Formula (I): R=phenyl

In a 12 L 3-neck round bottom flask (equipped with an ice/salt bath, a thermometer, dropping funnel, and a mechanical stirrer), N-phenylthiourea (734 g, 4.8 m), sodium molybdate dihydrate (5.0 g, 0.021 m), and sodium chloride 260 g, 4.5 m) were suspended in 2.5 L of water and cooled to about 0° C. Hydrogen peroxide (30%, 1710 g, 15.1 m) was added dropwise at a rate to maintain the temperature between 0-9° C. Once the addition was complete, the cooling bath was removed and the reaction slowly exothermed. The temperature of the reaction was controlled at about 35° C. with a cold water bath. Once the reaction exotherm was complete, the reaction was cooled to 10° C. and filtered. The filter cake was washed with a small amount of ice water. The sulfonic acid product was obtained as an off-white solid in 80% yield (766 g).

b. Formula (III): R=phenyl

In a 12 L 3-neck round bottom flask (equipped with a mechanical stirrer, a thermometer, and a cooling bath), morpholine (541 g, 6.3 m) in 3.5 L $CH_3CN$ was cooled and treated with glacial acetic acid (378 g, 6.3 m). The resulting slurry was cooled to 10° C. and the sulfonic acid prepared in Example 3a was added in one portion. In contrast to morpholine, the addition of the sulfonic acid to morpholine acetate is endothermic. Once the sulfonic acid was added, the cooling bath was removed. The reaction warmed to ambient temperature and once all of the solid had gone into the solution, the reaction was complete. The reaction was then concentrated to remove the $CH_3CN$. NaOH (50%, ~6.3 m) was diluted with 1.5 L of ice and added to the concentrate until the concentrate was neutral. The aqueous mixture was then extracted with ether and the ether phase was discarded. The aqueous phase was then treated with aqueous NaOH until very basic. A white solid precipitated from the solution. The solution was cooled, filtered, and washed with water. The product was isolated as a white solid in a 58% yield from phenylthiourea.

EXAMPLE 4 a. Formula (I): R=phenyl

In a 1-liter Morton flask (equipped with a mechanical stirrer and thermometer, cooled by a water/salt bath) 1-phenyl-2-thiourea (75 g, 0.49 m) and sodium molybdate dihydrate (0.19 g, 0.008 m) were suspended in 300 ml distilled water and cooled to 0° C. Hydrogen peroxide (113 ml, 1.0 m, 30%) was added dropwise at a rate to maintain the temperature below 5° C. Use of a Morton flask is recommended due to the ease in temperature control it provides. The reaction is initiated with a few milliliters of peroxide; once an exotherm or a color change (white to blue or green) is observed, addition of peroxide may continue. The addition of the first half of the peroxide is very exothermic; however, the addition of the second half is only mildly exothermic. For a successful experiment it is preferred that the temperature not exceed 5° C.; exotherms above about 10° C. result in impurities. Once the addition was complete, the reaction was stirred at 0°-10° C. for an additional 3.5-4.5 hrs. The reaction was filtered and the filter cake was washed two times with a small amount of ice water. The sulfinic acid product was obtained as a lightly colored solid and was used below as a wet cake.

b. Formula (III): R=phenyl

In a 1-liter 3-neck round bottom flask, morpholine (87.12 g, 1.0 m) in 600 ml acetonitrile was cooled and treated with glacial acetic acid (60.05 g, 1.0 m). The resulting slurry was cooled to about 10° C. and the sulfinic acid product of Example 4a was added in an endothermic reaction. The reaction mixture was stirred and allowed to warm to room temperature overnight. The reaction was checked by +1C(95:5:5; MeOH:CHCl$_3$ :HOAc; silica gel) and cooled to about 0° C. A white solid (morpholine acetate) precipitated and this was isolated by filtration. The filter cake was washed twice with a small amount of cold acetonitrile. The filtrate was concentrated (using a 30° C. bath or cooler) to approximately half the original volume (recovered 450 ml solvent) and then was treated with 25% NaOH until basic. The mixture (add water until all solid is in solution) was extracted 3 times (150 ml each) with methylene chloride; the organic phase was then washed with water (50 ml), dried over $Na_2SO_4$, and concentrated. There were obtained 68 g (68% yield) of product based on thiourea.

EXAMPLE 5

Formula (V): R=phenyl

In a 200 ml round bottom flask, N-methyl pyrrolidinone (15.6 g, 0.16 m) was treated with dimethyl sulfate (17.93 g, 0.14 m) and heated on a steam bath for 45 min. The reaction was cooled slightly. N-phenyl-1-morpholinecarboximidamine (14.11 g, 0.068 m) was dissolved in 60 ml hot methylene chloride and added to the complex formed above with stirring. A mild exotherm resulted. The reaction was heated at reflux for a half an hour. A check by tlc (silica gel: 95:5:5, MeOH:CHCl$_3$ :HOAc showed no starting material remained. The reaction was quenched into 250 ml 3 N NaOH and extracted 3 times with 50 ml $CH_2Cl_2$, dried over $K_2CO_3$ and concentrated to obtain the free base as a light brown/yellow oil. Fumaric acid (8.6 g, 0.074 m) was dissolved in 90 ml refluxing isopropanol. The free base prepared above was dissolved in 25 ml isopropanol and added to the fumaric acid with vigorous stirring. The solution was stirred and allowed to cool gradually to RT. A white precipitate formed which was collected by filtration. The filter cake was washed 2 times with a small amount of cold isopropanol. The product, linogliride fumarate, was obtained in an 86.5% yield as a white solid, mp 172°-175° C., softening at 165° C.

EXAMPLE 6 a. Formula (I): R=4-fluorophenyl 4-fluorophenyl thiourea (2.0 g, 0.0118 m) produced using a modified method of R. L. Frank et al. in Org. Syn., Collected Vol. 8, 735 (1955) and sodium molybdate dihydrate (0.004 g, 0.000018 m) were suspended in 10 ml of water. Hydrogen peroxide (3.6 ml, 30%, 0.035 m) was added dropwise at a rate to keep the temperature between 20°–25° C. Once the addition of the peroxide was complete, the cooling bath was removed and the reaction was allowed to exotherm to 28° C. The reaction was stirred for approximately six hours after which time it was cooled and filtered. The sulfonic acid product was obtained as a gray/brown solid in a 47% yield (mp 150° C., decomposition with gas evolution).

b. Formula (III): R=4-fluorophenyl

The sulfonic acid product of Example 6a (1.0 g, 0.00046 m) was added to morpholine (0.96 g, 0.011 m) and acetic acid (0.67 g, 0.011 m) in 8 ml acetonitrile at 5° C. The addition was endothermic and upon addition of the sulfonic acid, the reaction mixture turned purple. Within 1–2 min, the reaction turned bright blue. The ice bath was removed and the reaction sat overnight at room temperature. The reaction was treated with 3 N NaOH until very basic then extracted with CHCl$_3$, the organic phase was dried and concentrated. The green/brown oil crystallized to a solid upon storing at 0° C. The solid was suspended in water and filtered to yield 0.85 g (83% yield from sulfonic acid) of the desired product as a gray solid (mp 100° C. (soft) 105°–108° C. melt).

c. Formula (V): R=4-fluorophenyl

N-methylpyrrolidinone (0.38 g, 0.0038 m) was treated with dimethylsulfate (0.38 g, 0.003 m) and heated on a steam bath for 45 min. The guanidine product of Example 6b (0.5 g, 0.0022 m) was dissolved in 5 ml of CH$_2$Cl$_2$ with gentle warming and added to the complex formed above. The reaction mixture was stirred without external heat for 1.5 hrs (tlc showed reaction complete). The reaction was quenched into 3 N NaOH and extracted three times with CH$_2$Cl$_2$, dried over K$_2$CO$_3$ and concentrated. Fumaric acid (0.3 g, 0.0026 m) was dissolved in 7 ml refluxing IPA and was treated with the above isolate (dissolved in 3 ml IPA). The fumarate salt was obtained as a white solid in 70% yield (mp 170°–175° C.).

EXAMPLE 7 a. Formula (I): R=2-methylphenyl 2-methylphenyl thiourea (8.6 g, 0.05 m) and sodium molybdate dihydrate (0.02 g, 0.00008 m) were suspended in 30 ml of water. Hydrogen peroxide (30%, 16 ml, 0.157 m) was added dropwise at a rate to maintain the temperature between 20°–25° C. (cooling bath was used). Once the addition was complete, the reaction exothermed to 28° C. then cooled back to RT. The reaction sat at RT overnight. The reaction was cooled and filtered. The sulfonic acid product was obtained as a light blue solid in a 69% yield (mp 189°–192° C.).

b. Formula (III): R=2-methylphenyl

The sulfonic acid product of Example 7a (3.0 g, 0.014 m) was added to morpholine (2.4 g, 0.027 m) in 20 ml CH$_3$CN at RT. The reaction mixture was heated at 45° C. for 1 hr. The reaction was treated with 3 N NaOH until very basic and extracted with ether and methylene chloride, dried, and concentrated. A clear viscous liquid was obtained which solidified to a white semi-solid. 1.9 g of the desired product was obtained (62% yield).

c. Formula (V): R=2-methylphenyl

N-methylpyrrolidinone (1.1 g, 0.011 m) was treated with dimethylsulfate (1.18 g, 0.009 m) and heated on a steam bath for 40 min. The guanidine product of Example 7b (1.5 g, 0.007 m) was dissolved in 10 ml of CH$_2$Cl$_2$ and added to the complex at RT. The addition was exothermic and the reaction was complete within 0.5 hr. The reaction was quenched with 3 N NaOH and extracted 3 times with CH$_2$Cl$_2$, dried and concentrated. Fumaric acid (0.95 g, 0.008 m) was dissolved in 10 ml refluxing IPA and treated with the isolate (dissolving in 2 ml IPA). The final product was obtained in 48% yield as a white crystalline solid, mp 155°–157° C. with decomposition and gas evolution.

What is claimed is:

1. A N-arylformamidinesulfonic acid of the following formula (I):

wherein R is phenyl, methylenedioxyphenyl, phenyl substituted with from 1 to 3 halo substituents or phenyl substituted with a member selected from the group consisting of dimethylamino, methylethylamino, diethylamino, loweralkanoylamino, loweralkylthio, trifluoromethyl, hydroxy, benzyloxy, loweralkanoyloxy, loweralkanoyl and nitro.

2. The acid of claim 1, wherein R is phenyl substituted by a fluorine atom.

3. The acid of claim 2, wherein R is 4-fluorophenyl.

4. The acid of claim 1, wherein R is methylenedioxyphenyl or phenyl substituted with from 1 to 3 halo substituents.

5. The acid of claim 1, wherein R is phenyl substituted with a member selected from the group consisting of dimethylamino, methylethylamino, diethylamino, loweralkanoylamino, loweralkythio, trifluoromethyl, hydroxy, benzyloxy, lower alkanoyloxy, lower alkanoyl and nitro.

* * * * *

UNITED STATES PATENT AND TRADEMARK OFFICE
CERTIFICATE OF CORRECTION

PATENT NO. : 4,693,850

DATED : September 15, 1987

INVENTOR(S) : Cynthia A. Maryanoff et al.

It is certified that error appears in the above-identified patent and that said Letters Patent is hereby corrected as shown below:

Column 10, line 39, "phenyl", 1st occurrence should be deleted.

Signed and Sealed this

Ninth Day of February, 1988

Attest:

DONALD J. QUIGG

Attesting Officer

Commissioner of Patents and Trademarks